United States Patent [19]

Smid et al.

[11] Patent Number: 5,093,502
[45] Date of Patent: Mar. 3, 1992

[54] 14α,17α-DIHYDROXY-17β-SUBSTITUTED STEROIDS

[75] Inventors: Peter M. Smid, Bleiswijk; Willem J. Van Zoest, Schiedam; Pieter G. Weber; Arthur F. Marx, both of Delft, all of Netherlands

[73] Assignee: Akzo NV, Arnhem, Netherlands

[21] Appl. No.: 484,455

[22] Filed: Feb. 16, 1990

Related U.S. Application Data

[63] Continuation of Ser. No. 818,233, Jan. 10, 1986, abandoned.

[30] Foreign Application Priority Data

Jan. 14, 1985 [EP]  European Pat. Off. ........ 85200022.3

[51] Int. Cl.$^5$ ............................................ C07D 339/08
[52] U.S. Cl. .......................................... 549/11; 549/4; 549/14; 549/15; 549/22; 549/30; 549/31; 552/505; 552/515; 552/521; 552/522; 552/558; 552/560; 552/561; 552/562; 552/563; 552/582

[58] Field of Search ............... 552/540, 548, 553, 557, 552/582, 632, 505, 515, 521, 522, 558, 560, 561, 562, 563, 582; 549/336, 4, 13, 20, 35, 14, 15, 22, 30, 31

[56] References Cited

U.S. PATENT DOCUMENTS 3,243,355  3/1966  Holmlund .......................... 435/872
4,557,867  12/1985  Campbell .......................... 260/239.5
4,600,538  7/1986  Walker .......................... 260/397.45

OTHER PUBLICATIONS

Beloeil, J. C., CA: 98:107606c "Stereochemistry of Gaseous Anions . . . ", Mar. 28, 1983.
Beloeil, J. C., Tetrahedron, vol. 39, No. 23, p. 3937 (1983).

Primary Examiner—Mary C. Lee
Assistant Examiner—Jacqueline Haley
Attorney, Agent, or Firm—William M. Blackstone

[57] ABSTRACT

A process for the preparation of novel 14α, 17α-dihydroxy-17β-substituted steroids by reacting 14α-hydroxy-17-oxo-steroids with metal organic compounds and the use of the said novel steroids in the production of 14α, 17α-methylenedioxy-pregnane derivatives.

4 Claims, No Drawings

14α,17α-DIHYDROXY-17β-SUBSTITUTED STEROIDS

This is a continuation of application Ser. No. 06/818,233, filed Jan. 10, 1986.

STATE OF THE ART

Steroids occur widely in nature, both in animals and plants. Many steroids are hormones such as estrogens and cortisone which are produced by the body's endocrine system and are of great importance in the regulation of numerous body processes such as growth and metabolism.

Over the last 35 to 40 years, steroid therapy or the medical augmentation of steroid hormone insufficiencies in the body has been one of the major chapters in the history of medical progress. Steroids are used now as anti-inflammatory agents, anti-allergic agents, anabolic agents, diuretics and contraceptives among other uses. For a long time, steroids for medical use were prepared starting with the isolation of steroids from natural sources followed by partial chemical degradation and one or more chemical reactions to obtain the desired substituent pattern. The oldest examples of steroids isolated from natural sources, which are still important as starting material for the preparation of steroids for medical use, are cholesterol, lanosterol and cholic acids. Since then, hecogenin and diosgenin became important raw materials too.

At the present time, cheap starting materials for the synthesis of pharmaceutically active steroids are available by microbiological degradation of natural steroids. Especially a number of 17-oxo-steroids can be made by degradation of the abundant soybean derived sterols, sitosterol and campesterol in this way. 17-oxo-steroids which may be prepared in this way are for instance $\Delta^4$-androstene-3,17-dione and $\Delta^4$-androstadiene-3,17-dione which derivatives can be converted into other steroid compounds in a manner known in the art.

In British Patent No. 1,218,282, 14α,17α,-methylene-dioxy-pregnane derivatives of the formula

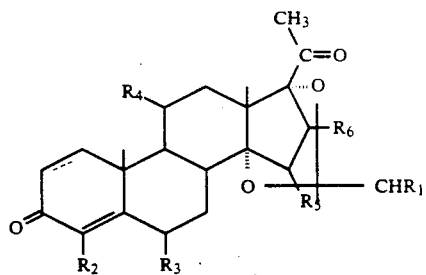

are described.

Compounds of formula I are therapeutically active compounds possessing progestational activity and some of the compounds are particularly useful in the treatment of threatened abortus, of dysmenorrhoea and for healing the mucous membrane of the uterus. Moreover, many of these compounds have excellent contraceptive properties and give in many cases a remarkable long lasting protection against conception. Therefore, they may be administered as long-lasting contraceptives and proligestone of formula II is especially very suitable as a long-acting contraceptive because of its good anti-gonadotrophic activity, its weak progestogenic activity and the absence of any androgenic activity.

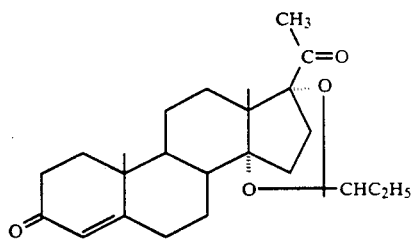

The pregnane derivatives of formula I may be prepared by reacting a 14α,17α-dihydroxy-pregnane with an aldehyde of the formula $R_1CHO$ or an acetal thereof of the formula $R_1CH(OR_7)_2$ in which $R_7$ is an alkyl.

The 14α,17α-dihydroxy-pregnane derivatives used as starting materials in the processes hereinbefore described can be obtained by microbiological processes from the corresponding 17α,-hydroxy-pregnanes. For this process, microorganisms that are capable of introducing a hydroxyl group at the 14-position are used and various strains of the genera Curvularia, particularly Curvularia lunata, Helicostylum and Absidia regnieri, have been found to be very suitable in this respect (see, for example, British Patent No. 1,105,980). The said 14α,17αa-dihydroxy-pregnane derivatives can also be prepared from Reichstein's compound S, i.e. 17α,121-dihydroxy-$\Delta^4$-pregnene-3,20-dione by microbiological conversion of this compound, e.g. with Curvularia lunata, into 17α,14α,21-trihydroxy-$\Delta^4$-pregnene-3,20-dione followed by reductive removal of the 21-hydroxy group. [Tetrahedron Supp No. 7 (1966), p. 325]. The 14α,17α-dihydroxy-4-pregnene-3,20-dione thus obtained may be converted into other pregnane derivatives by manners known per se. It has appeared, however, that in practice the above described preparations of the dihydroxy starting materials are not entirely suitable.

As already described above 14α-hydroxy groups may be introduced into the steroid molecule by microbiological processes. Microbiological 14α-hydroxylation of 17-oxo-steroids, has been described, for example in Japanese Patent Application Serial No. 6341/65, U.S. Pat. No. 3,243,355 and Dutch Patent Application Serial No. 6715404.

OBJECTS OF THE INVENTION

It is an object of the invention to provide a novel process for the preparation of 14α,17α-dihydroxy-17β-substituted steroids starting from inexpensive compounds and novel compounds produced thereby.

It is another object of the invention to provide a novel process for the production of 14α,17α-dihydroxy-17β-acyl steroids.

These and other objects and advantages of the invention will become obvious from the following detailed description.

THE INVENTION

It has now been found that 14'-hydroxy-17oxo-steroids obtainable by microbiological 14a-hydroxylation of 17-oxo-steroids can easily be converted into 14α,17αdihydroxy-17β-substituted steroids by reaction with certain metal organic compounds. The present invention, therefore, relates to a process for the preparation of 14α,17α-dihydroxy-17β-substituted steroids by reacting a 14α-hydroxy-17-oxo-steroid and a metal organic compound in which the metal is lithium, sodium or potassium or a Grignard compound.

Nucleophilic addition at the 17-keto group of steroids is known. For instance, the reaction of 17-keto steroids with hydrogen cyanide or acetone cyanohydrin to form a mixture of 17-cyano-17-hydroxy compounds is well known and another example of nucleophilic addition is the reaction of a 17-keto steroid with a Grignard reagent to form a 17-alkyl-17-hydroxy steroid. The stereoisomer formed in this reaction is predominantly the 17α-alkyl-17β-hydroxy compound. For instance, the orally effective androgen, 17α-methyl-testosterone, is prepared from 3β-hydroxy-Δ⁵-androsten-17-one by treatment with methyl magnesium iodide to obtain the 17α-methyl derivative which is then oxidized. From large scale experiments, the epimeric 3β,17α,-dihydroxy-17β-methyl-Δ⁵-androstene could be isolated as a by-product. Reaction of 17-keto steroids with benzyl magnesium chloride and allyl magnesium bromide resulted in the formation of 17β-hydroxy-17α-substituted derivatives. It can be concluded, therefore, that attack from the a-side of the molecule is preferred.

It has appeared that the steric course of the alkylation of 17-keto steroids is not influenced by an 11-keto group but the presence of a 12α-OH group as well as a 16α-acetoxy group renders α-side approach to the 17-oxo-group more difficult (Organic Reactions in Steroid Chemistry, Van Nostrand Reinhold Company, New York Vol. 2, pg. 64). However, the reaction of 3β-acetoxy-14α-hydroxy-Δ⁵-andro-stene-17-one with allyl magnesium bromide resulted in only one isomer 3β,14α,17β-trihydroxy-17α-allyl-Δ⁵-androstene [Recl. trav. chim. Pays Bas, Vol. 82, p. 149 (1963)]. It may be concluded, therefore, that the presence of a 14α-hydroxy group has little or no influence on the steric course of the reaction, and certainly does not make approach from the β-side of the steroid more favorable. In view of the above mentioned facts that attack from the α-side of the molecule is preferred and that the presence of an 14α-hydroxy group hardly influences the steric course of the reaction, it was to be expected that all nucleophiles attacking the 17-keto-group would result in 17β-hydroxy-17α-substituted steroids when using 14α-hydroxy steroids.

The process of the present invention surprisingly resulted in the formation of the isomer at the 17-site of the steroid molecule wherein the nucleophile has come from the β-side of the molecule, thus exclusively resulting in 14α,17α-dihydroxy-17β-substituted steroids. The presence of a 14α-hydroxy group and a 17α-hydroxy group makes the new process of the invention suitable for the preparation of the 14α,17α-methylenedioxy-pregnane derivatives described in British Patent No. 1,218,282, particularly when those nucleophiles are chosen which can be converted simply into an acetyl group. An exception, however has to be made for the reaction of the 17-keto-steroid with methyl magnesium iodide as this reaction resulted in the formation in low yields of a 14α,17β-dihydroxy-17α-methyl compound. In this respect, it has to be remarked that the reaction of the 17-keto-steroid with methyl lithium results in the formation of the desired 14α,17α-dihydroxy compound. Using ethyl magnesium bromide, the desired compound was obtained in a low yield. The undesired stereo-isomer could also be isolated from the reaction mixture also in a low yield. Further, using allyl magnesium bromide, the desired compound was obtained which is in contradiction with the results obtained in the literature [Recl. Trav. Chim. Pays Bas Vol. 82, p. 149 (1962)].

The invention therefore relates to the preparation of 14α, 17α-dihydroxy-17β-substituted steroids by reaction of a 14α-hydroxy-17-oxo-steroid with a metal organic compound, for instance an alkali metal acetylide and other organolithium, organosodium or organopotassium compounds, with the proviso that the metal organic compound is not a methyl magnesium halide compound.

Suitable metal-organic compounds are compounds with the formula R-M in which R is alkyl, 1-alkenyl or 1-alkynyl which optionally may contain a double bond and which optionally may be substituted by at least one substituent and M is lithium, sodium or potassium/or a Gringnard compound Preferably R is alkyl of 1to 6 carbon atoms, preferably methyl or ethyl, 1-alkenyl of 2 to 6 carbon atoms, preferably ethenyl, or 1-alkynyl of 2 to 6 carbon atoms, preferably ethynyl, which groups may be substituted by at least one alkoxy of 1 to 4 carbon atoms, tetrahydropyranyloxy, alkylthio of 1 to 4 carbon atoms, arylthio, alkylsulfinyl of 1 to 4 carbon atoms, arylsulfinyl, alkylsulfonyl of 1 to 4 carbon atoms, arylsulfonyl, dialkylamino of 1 to 4 carbon atoms, alkylarylamino of 1 to 4 carbon atoms, diarylamino, alkylhydrazono of 1 to 6 carbon atoms, alkyleneoxythio of 1 to 4 carbon atoms, alkylenethiosulfoxy of 1 to 4 carbon atoms aralkylenedithio or a 1-(tri-$C_{1-4}$ alkylsilyloxy) or di-dialkylamino of 1 to 6 carbon atoms together with 1-cyano, the aryl groups preferably being phenyl or naphthyl optionally substituted by methyl. Preferably, R is ethyl, ethenyl or ethynyl optionally substituted by at least one alkyl of 1 to 4 carbon atoms, phenyloxy, alkylthio of 1 to 4 carbon atoms, phenylthio, alkylsulfinyl of 1 to 4 carbon atoms, phenylsulfinyl, alkylsulfonyl of 1 to 4 carbon atoms, phenylsulfonyl, dialkylamino of 1 to 4 carbon atoms, alkyl-phenylamino of 1 to 4 alkyl carbon atoms, diphenylamino, alkyleneoxthio of 1 to 4 carbon atoms, alkylenethiosulfoxy or alkylenedithio of 1 to 4 carbon atoms, the phenyls optionally substituted by methyl group, or by 1-(tri-$C_{1-4}$ alkylsilyloxy) together with a 1-cyano.

In particular, those groups of R are preferred which can be hydrolyzed into an acyl group, especially an acetyl group, and acetylides, which also can be converted into acyl groups. The first of these groups is known in literature as the group of masked carbonyl groups, more particularly "umpolugs" reagents.

Preferred organometallic compounds are therefore those groups in which R is ethyl substituted at the 1 position by two groups chosen from alkoxy of 1 to 4 carbon atoms, phenyloxy, alkylthio of 1 of 4 carbon atoms, phenylthio, alkylsulfinyl of 1 to 4 carbon atoms, phenylsulfinyl, alkylsulfonyl of 1 to 4 carbon atoms, and phenylsulfonyl, or 1-cyano together with a tri-($C_{1-4}$alkylsilyloxy) or substituted at the 1 position with an alkyleneoxythio of 1 to 4 carbon atoms, alkylenethiosulfoxy of 1 of 4 carbon atoms, or alkylene-dithio, the phenyls optionally substituted with kethyl, or R is ethenyl substituted at the 1-opposition by a group chosen from alkoxy of 1 to 4 carbon atoms, phenyloxy, alkylthio of 1 of 4 carbon atoms, phenylthio, alkylsulfinyl of 1 to 4 carbon atoms and phenylsulfonyl, the phenyl optionally substituted by methyl, or R is ethynyl. In case R is an acetylide, it is preferred to use lithium acetylide, especially in combination with ethylenediamine.

Suitable starting steroids for the process of the invention are 14α-hydroxy-17-oxo-steroids of the formula

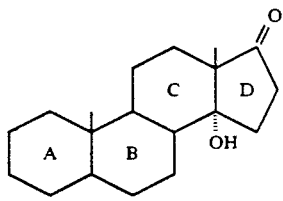
III in which the A,B,C and D rings optionally contain at least one double bond, are optionally substituted by at least one hydroxy, amino, oxygen, or alkoxy or alkoxyalkoxy groups and are optionally disubstituted by at least one alkylenedioxy, alkylenedithio, alkylene-thiosulfoxy or alkyloxythio.

When the A,B,C and D rings contain one or more double bonds, these double bonds are preferably present between $C_1$ and $C_2$, $C_3$ and $C_4$, $C_4$ and $C_5$, $C_5$ and $C_6$, $C_6$ and $C_7$, $C_9$ and $C_{11}$ and/or $C_{11}$ and $C_{12}$. More preferably, the double bond is present between $C_4$ and $C_5$ When two or more double bonds are present in the following systems are especially preferred: $C_{13}$-$C_4$ and $C_5$-$C_6$ and Cl-C2 and $C_4$-$C_5$ group, suitable groups are 3-, 9-, 11- or 12-hydroxy. When the A,B, C and D rings are substituted by an amino, suitable aminos are 3-alkylaminos preferably containing 1-4 carbon atoms, 3-dialkylaminos wherein alkyls are the same or different, each alkyl preferably containing 1 to 4 carbon atoms, or aminos in which the nitrogen atom together with the alkyl form a heterocyclic ring preferably containing 5 to 8 ring atoms, which ring optionally may contain an oxygen atom. Particularly preferred are dimethylamino, diethylamino, pyrolidino and morpholino.

When the A,B,C, and D rings are substituted by an oxygen atom, suitable oxygen atoms are at $C_3$, $C_{11}$ or $C_{12}$ preferably at C3. When the A,B,C and D rings are substituted by an alkoxy, suitable alkoxys are 3-, 9-, 11- or 12- alkoxy of 1 to 4 carbon atoms, preferably 3-methoxy or ethoxy. When A,B,C and D rings are substituted by alkoxyalkoxy, suitable are3-methoxymethoxy, methoxymethoxy or tetrahydro-pyranloxy.

When the A,B,C and D rings are disubstituted, suitable substituents are 3,3-alkylenedioxy, 3,3-alkylenedithio, 3,3-alkylenethio-sulfoxy or 3,3-alkyleneoxythio. The alkylene group preferably contains or 3 carbon atoms.

More particularly the invention relates to compounds which contain a 3-keto and double bonds between $C_1$ and $C_2$ and/or $C_4$ and $C_5$, or contain functional groups which can be converted into the keto group and double bond mentioned before. Preferred are 14α-hydroxy-$\Delta^{1,4}$-androstene-3,17-dione and 14α-hydroxy-$\Delta^{1,4}$-androstadiene-3,17-dione.

Those steroids which contain one or more groups which would interfere during the reaction have to be protected at the relevant position and this can be done by methods known in the art. In this respect, a 3-oxo or a 3-oxo-$\Delta^4$ group always have to be protected and this can be done, for instance, by converting the 3-oxo group into an enol ether or an enamine derivative, or by conversion of the 3-oxo group into an alkylenedioxy, alkylenedithio or alkyleneoxythio.

The reaction between the carbon nucleophile and the 14α-hydroxy-17-oxo-steroid is carried out in an inert organic solvent medium and suitable solvents are, for example, ethers such as tetrahydrofuran, diethyl ether, 1,2-dimethoxyethane, 1,2-diethoxyethane and dioxane,, aromatic hydrocarbons such as benzene, toluene and xylene., aliphatic hydrocarbons such as pentane, hexane and cyclohexane, tetramethylethylenediamine and hexamethylphosphoric acid triamide and mixtures thereof. Preferred solvents are tetrahydrofuran and dioxane. During the reaction the temperature is maintained between −80° C. and 50° C., preferred between −30° C. and 30° C..

Another feature of the invention is the new 14α,17α-dihydrox −17β-substituted compounds which can be prepared by the process of the invention. Therefore, the invention also relates to 14α,17α-dihydroxy-17β-substituted steroids of the formula

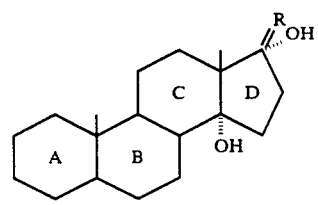
IV wherein R is as defined above and the substituents of the steroid molecule are also as defined above.

Preferably those carbon nucleophiles are used having a group R which can be converted into an acyl group and therefore, R preferably is alkyl, especially ethyl substituted as described above, a 1-alkenyl especially ethenyl substituted as described above, or alkynyl, especially ethynyl.

The conversion of the said R into an acyl may be performed by methods known in the art. As a general rule, the alkyl and 1-alkenyl described in the paragraphs above may be hydrolyzed under aqueous acidic conditions and the conversion of an alkynyl is generally performed using metal-ions, preferably mercury (II) compounds. For the conversion of the compounds of formula IV having a R which may be converted into an acyl into compounds having the formula

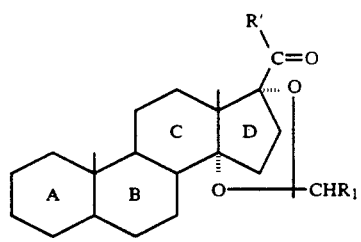
V wherein R' is the remainder of R after hydrolysis into the 17β-acyl group, $R_1$ is an aliphatic hydrocarbon having less than 10 carbon atom optionally substituted by halogen or a carboxyl or methoxycarbonyl, an aryl optionally substituted by a halogen or alkyl of 1 to 6 carbon atoms, nitro or amino or at least one lower alkoxy or an arylalkyl of 1 to 6 alkyl carbon atoms, cycloalkyl of 3 to 8 carbon atoms, lower alkoxy or furyl and the substituents of the steroid part of the molecule are as defined above, it is possible to use two different processes.

In the first process, the 14α,17α-dihydroxy-17βsubstituted steroid is reacted with an aldehyde of the formula $R_1CHO$ or an acetal thereof or a suitable orthoformate followed by conversion of the R into an acyl group. In the second process; the R is first converted into the acyl followed by reaction with the aldehyde of formula R₁CHO or an acetal thereof or a suitable orthoformate.

In this respect, in case that one or more protective groups are present in the steroid skeleton due to the fact that otherwise one or more substituents would be present which would interfere in the reaction of the carbon nucleophile and the 17-oxo, these groups may be removed immediately after the reaction as well as after the conversion of R into an acyl or after the reaction with the aldehyde or an acetal thereof or a suitable orthoformate. Sometimes, it is possible to remove the protective groups simultaneously with the conversion of R into the acyl.

It will be appreciated that the use of the compounds of formula IV having a R which may be converted into an acyl for the preparation of compounds of formula V forms a feature of the invention, especially for the use of these compounds for the preparation of proligestone, 14α,17α-propylidenedioxy-Δ⁴-pregnene-3,20-dione and related compounds. The invention, therefore, also relates to the preparation of compounds of formula V starting from a compound of formula IV whereby R' is the remainder of R after hydrolysis into the 17β-acyl wherein R is defined as above, the substituents of the steroid molecule are as defined above and R₁ is an aliphatic hydro-carbon group having less than 10 carbon atom optionally substituted by halogens or carboxyl or methoxycarbonyl, an aryl group optionally substituted by halogen, or alkyl of 1 to 6 carbon atoms, nitro or amino or by one or more lower alkoxy or an arylalkyl of 1 to 6 carbon atoms, a cycloalkyl of 3 to 8 carbon atoms, lower alkoxy or furyl.

For the preparation of proligestone, 14α-hydroxy-Δ⁴-andros-tene-3,17-dione is used as the starting compound. The 3-oxo-Δ⁴ moiety of this molecule has to be protected, for instance, by conversion into a compound of the formula

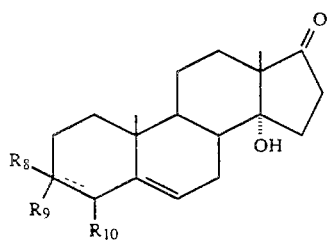

VI wherein R₈ and R₉ are the same or different and each is -ORll in which R is alkyl of 1 to 6 carbon atoms optionally substituted with alkoxy of 1 to 4 carbon atoms or R₈ and R₉ together are an alkylene-dioxy of 2 to 4 carbon atoms, alkylenedithio of 2 to 4 carbon atoms, alkylenethiosulfoxy of 2 to 4 carbon atoms or alkyleneoxythio of 2 to 4 carbon atoms and R₁₀ is hydrogen, or R₈ is OR₁₁ or

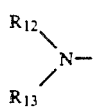

wherein R₁₂ and R₁₃ are the same or different and each is alkyl, or R₁₂ and R₁₃ together with the nitrogen atom to which they are attached form a 5- or 6-membered heterocyclic which may contain a further hereto atom in the ring and R₉ and R₁₀ together form an additional bond in the 3–4 position. Preferably, R is OR₁₁ in which R₁₁ is alkyl of 1 to 6 carbon atoms, especially methyl or ethyl, and R₉ and R₁₀ together are an additional double bond.

For the preparation of proligestone, it is preferred to use for the preparation of the intermediate compounds of formula IV a metal organic compound chosen from the group lithium, sodium or potassium acetylide, especially lithium acetylide which is preferably used in combination with a complexing agent, for instance diaminoethane, 1-alkali metal 1,1-trimethylenedithio-ethane, preferably the lithium derivative, 1-alkali metal-1-alkylthio of 1 to 6 carbon atoms-ethene, preferably the lithium derivative and methyl or ethyl, 1-alkali metal-1-phenylthio-ethene, preferably the lithium derivative the phenyl optionally substituted with methyl, 1-alkali metal-1-phenyl-sulfinyl-ethene, preferably the lithium derivative, the phenyl optionally substituted with methyl, 1-alkali metal-1-phenylsulfonyl-ethene, preferably the lithium derivative, the phenyl optionally substituted with methyl, 1-alkali metal-1-alkoxy of 1 to 6 carbon atoms-ethene, preferably the lithium derivative and methyl or ethyl and 1-alkali metal-1-phenoxy-ethene, preferably the lithium derivative, the phenyl optionally substituted with methyl.

The compounds formula IV as described in the preceeding paragraph may be converted into proligestone by hydrolysis of R into an acetyl group followed by reaction with propionaldehyde, or by reaction with propionaldehyde followed by hydrolysis of R into an acetyl group. The conversion of the protected 3-oxo-Δ⁴ group into the 3-oxo-Δ⁴ may after the reaction with the metal organic compound, or after the reaction with propionaldehyde, or after the hydrolysis of R. In some cases, the hydrolysis of R also results in the removal of the protective group.

In the following examples there are described several preferred embodiments to illustrate the invention. However, it is to be understood that the invention is intended to be limited only as defined in the appended claims.

EXAMPLE 1

3-Methoxy-Δ³,⁵-androstadien-14α-ol-17-one 90 g (0.30 mol) of Δ⁴-androstene-14α-ol-3,17-dione were suspended in a mixture of 90 ml (0.82 mol) of trimethylorthoformate and 90 ml (2.2 mol) of methanol. 0.5 ml of sulfuric acid in methanol (5% v/v) was added under vigorous stirring and after stirring for 2 hours at 25° C., 0.5 ml of triethylamine was added. The solid mass was filtered, washed with methanol and dried to obtain 88.8 g (94% yield) of 3-methoxy-Δ³,⁵-androstadien-14α-ol-17-one NMR (CDCl₃, DMSO d₆) delta 0.975 (6H, s), 2.88 (1H, s), 3.55 (3H, s), 5.15 (1H, s), 5.26 (1H, m).

EXAMPLE 2

3-Ethoxy-Δ³,⁵-androstadien-14α-17-one

Using the procedure of Example 1, triethylorthoformate was used instead of trimethylorthoformate to obtain a 93% yield of 3-ethoxy-Δ³,⁵-androstadien-14a-ol-17-one. NMR (CDCl₃, DMSO d₆) delta 1.003 (6H, s), 1.28 (3H, tr), 3.11 (1H, s), 3.73 (2H, q), 5.10 (1H, s), 5.21 (1H, m).

EXAMPLE 3

3-Ethoxy-17β-ethynyl-Δ$^{3,5}$-androstadiene-14c,17β-diol 30 g (90.9 mmol) of 3-ethoxy-14α-hydroxy-androstadiene-Δ$^{3,5}$-17-one and 30 g (320 mmol) of lithium acetylide-ethylenediamine complex in 180 ml of dry dioxane were stirred for 20 hours at 25° C. under a nitrogen atmosphere. After careful addition of 250 ml of water at 0° C., the reaction mixture was stirred for half an hour during which a product crystallized. The solid mass was filtered, washed with water/dioxane (50/50), acetic acid (10% in water) and water, and dried to obtain 3-ethoxy-17β-ethynyl-Δ$^{3,5}$-androstadiene-14α,17α-diol.

NMR (CDC13) delta 1.002 (3H, s), 1.059 (3H, s), 1.31 (3H, tr), 2.48 (1H, s), 3.12 (1H, s), 4.18 (1H, s), 3.80 (2H, q), 5.15 (1H, m), 5.25 (1H, s).

EXAMPLE 4

17β-ethynyl-Δ$^4$-androsten-14α,17β-diol-3-one

The reaction product of Example 3 was suspended in a mixture of 150 ml of acetic acid and 50 ml of water. 30% sulfuric acid was added to obtain a pH of 0.5 and after stirring for 1 hour at 25° C., a solution of sodium hydroxide was added to neutralize the acid. 250 ml of water was added. The crystallized compound was filtered, washed with acetic acid/water (50%) and dried to obtain 28 g (92% yield calculated on 3-ethoxy-Δ$^{3,5}$-androstadien-14α,ol-17-one) of 17β-ethynyl-Δ$^4$-androsten-14α,17β-diol-3-one.

NMR (CDCl$_3$): delta 1.051 (3H, s), 1.206 (3H, ls), 2.51 (1H, s), 3.84 (1H, s), 4.45 (1H, s), 5.73 (1H, s).

EXAMPLE 5

17β-Ethynyl-14α,17α-propylidenedioxy-Δ$^4$-androsten-3-one

The reaction product of Example 4 was reacted with 18 ml of propanal and 1 ml of 30% sulfuric acid in acetic acid in 50 ml of acetic acid at 25° C. for 1 hour. After addition of 75 ml of water and 3 ml of sodium hydroxide solution (15% in water), the crystallized mass was filtered and crystallized from 200 ml of methanol to obtain 25.2 g (90% yield) of 17β-ethynyl-14α,17β-propylidene-dioxy-Δ$^4$-androsten-3-one. NMR (CDCl$_3$): delta 0.94 (3H, tr), 1.023 (3H, s), 1.195 (3H, s), 2.51 (1H, s), 4.88 (1H, tr), 5.77 (1H, s).

EXAMPLE 6

14α,17α-Propylidenedioxy-Δ$^4$-pregnene-3,20-dione 5 g (13.6 mmol) of the reaction product of Example 5 were suspended in 30 ml of acetic acid, 6 ml of water, and a solution of 0.75 ml of sulfuric acid in acetic acid (30% v/v) and 300 mg (1.38 mmol) of mercury (II) oxide were added. The reaction mixture was stirred for 2 hours at 50° C. and cooled to 0° C., after which 2 ml of 5% sodium hydroxide solution and water were added. The crystallized mass was filtered, washed with 25% acetic acid in water, dried and crystallized from methanol to obtain 3.84 g (73% yield) of 14α,17α-propylidenedioxy-Δ$^4$-pregnene-3,20-dione.

NMR (CDCl$_3$): delta 0.843 (3H, s), 0.96 (3H, tr), 1.178 (3H, s), 2.14 (3H, s), 4.86 (1H, tr), 5.68 (1H, s).

EXAMPLE 7

Δ$^4$-pregnene-14α,17β-diol-3,20-dione 2 g (6.1mm) of 17β-ethynyl-Δ$^4$-androsten-14o,17c-diol-3-one were suspended in a mixture of 20 ml of acetic acid, 4 ml of water and 0.5 ml of a solution of sulfuric acid in acetic acid (30% v/v) and 240 mg of mercury (II) oxide (1.11 mmol) were added. The reaction mixture was stirred for 2 hours at 30° C. and 0.5 ml of 15% sodium hydroxide solution was added followed by 10 ml of water. The crystallized mass was filtered, washed and dried to obtain 1.44 g of Δ$^4$-pregnene-14α,17α-diol-3,20-dione (68% yield). NMR (CDCl$_3$, CD$_3$OD): delta 0.77 (3H, s), 1.25 (3H, s), 2.22 (3H, s), 4.32 (2H, s), 5.73 (1H, s). The compound could be converted into 14α,17α-propylidenedioxy-Δ$^4$-pregnene-3,20-dione by known methods.

EXAMPLE 8

3-Ethoxy-17β-1-(1-thioethenyl)-Δ$^{3,5}$-androstadiene-14α,17α-diol

To a solution of 20 ml of phenylthioethane and 2 ml of diisopropylamine in 200 ml of dry THF under a nitrogen atmosphere, 100 ml of 15% n-butyllithium in hexane were added over 30 minutes at −10° C. After stirring for 20 minutes, the temperature was raised to 20° C. and 10 g (30.3 mmol) of solid 3-ethoxy-Δ$^{3,5}$-androstadien-14α-17-one were added. The reaction mixture was stirred for 30 minutes, cooled in ice-water and 100 ml of water were carefully added. The organic layer was separated and was washed with water and dilute acid. The aqueous layer was extracted with toluene and the combined organic layers were dried and evaporated in vacuo. 200 ml of hexane were carefully added to the residue and after cooling at 0° C. for 30 minutes, the crystallized mass was filtered, washed with hexane and dried. Hydrolysis of the 3-ethoxy resulted in 17β-1-(1-phenylthioethenyl)-Δ$^4$-androsten-14α,17α-diol-3-one.

NMR (CDCl$_3$, CD$_3$OD): delta 0.98 (3H, s), 1.27 (3H, s), 4.20 (2H, s), 4.78 and 5.51 (2H, 2s), 5.87 (1H, s), 7.1 (5H, m).

EXAMPLE 9

14α,17α-Propylidenedioxy-idenedioxy-Δ$^4$-pregene-3,20-dione 14α,17β-Propyl

The reaction product of Example 8 was dissolved in 60 ml of methylene chloride and 60 ml of acetic acid, 6 ml of water and 3 ml of a solution of sulfuric acid in acetic acid (10% v/v) were added. After stirring for 3 hours, 2 ml of a 50% sodium hydroxide solution were added and methylene chloride was evaporated in vacuo, followed by addition of 250 ml of water to the residue. The crystallized mass was filtered and washed twice with 10 ml of acetone. The compound had a NMR spectrum which was identical with the compound prepared in Example 7. The crude reaction product was converted into 14α,17α-propylidenedioxy-Δ$^4$-pregnene-3,20-dione by known methods to obtain 4.53 g (39% yield calculated on 3-ethoxy-Δ$^{3,5}$-androstadien-14α-17-one). The compound was identical with the compound of Example 6.

EXAMPLE 10

3-Ethoxy-17β-1-(1,1-trimethylenedithioethyl)-Δ$^{3,5}$-androstadiene-14α,17α-diol To a solution of 20 ml of 1,1-trimethylenedithioethane (2-methyl-1,3-dithiane) in 200 ml of dry THF under a nitrogen atmosphere, 100 ml of 15% n-butyllithium is hexane were added over 15 minutes at −50° C. and after stirring for 1 hour at 0° C. 15 g (45.45 mmol) of solid 3-ethoxy-Δ$^{3,5}$-androstadien-14-ol-17-one were added. The reaction mixture was stirred at 30 minutes at 0° C. and 200 ml of water were added. The reaction mixture was extracted with toluene and the organic layer was washed with water, dried and evaporated in vacuo. 150 ml of hexane were carefully added to the residue and the crystallized mass was filtered after 10 hours, washed with hexane methylenedithioethyl)-Δ$^4$-androsten-14c,17β-diol-3-one. NMR (CDCl$_3$): delta 1.210 (6H, s), 2.0 (3H, s), 4.45 (2H, s), 5.70 (1H, s).

EXAMPLE 11

Δ$^4$-pregnene-14α,17α-diol-3,20-dione

The reaction product of Example 10 was reacted by the method of Example 9 and the product was identical with the product of Example 7. The isolated product was converted into 14α,17α-propy-lidenedioxy-Δ$^4$-pregnene-3,20-dione to obtain 9.45 g (54% yield calculated on 3-ethoxy-Δ$^{3,5}$-androstadien-14α-ol-17-one). The product was identical to the product of Example 6.

EXAMPLE 12

3-Ethoxy-17β-1-(1-ethoxy-ethenyl)-Δ$^{3,5}$-androstadiene-14α,17α-diol 200 ml of 15% n-butyllithium in hexane were concentrated by distillation of 100 ml of hexane under a nitrogen atmosphere and 250 ml of THF were added to the residue at 0° C. Ethyl vinylether was added to the THF over 10 minutes and the reaction mixture was refluxed for 20 minutes, cooled to 25° C. 10 g (30.3 mmol) of solid 3-ethoxy-Δ$^{3,5}$-androstadien-14α-17-one were added and the reaction mixture was stirred for 30 minutes. 100 ml of water were added at 0° C. and the organic layer was separated and washed with water and ammonium chloride solution. The aqueous layer was extracted with toluene and the combined organic layers were washed, dried and evaporated in vacuo to obtain 3-ethoxy-17β-1-(1-ethoxy-ethenyl)-Δ$^{3,5}$-androstadiene-14α,17α-diol, as a white, solid mass.

EXAMPLE 13

Δ$^4$-pregnene-14α,17α-diol-3,20-dione

The reaction mixture of Example 12 was reacted by the method of Example 9 and the isolated compound was converted into 14α,17α-propylideneioxy-Δ$^4$-pregnene-3,20-dione in a yield of 7.49 g (65% calculated on 3-ethoxy-Δ$^{3,5}$-androstadien,-14α-ol-17-one). The isolated compounds were identical with the products of Example 6 and 7, respectively.

EXAMPLE 14

17β-1-(1-ethoxyethenyl)-Δ$^4$ -androsten-14α,17α-diol-3-one

15 To a solution of 50 ml of ethyl vinylether in 50 ml of dry THF under a nitrogen atmosphere, 100 ml of 15% n-butyllithium in hexane were added and after refluxing for 20 minutes, 5 g (14.1 mmol) of solid 3-3(N-morpholino)-Δ$^{3,5}$-androstadien-14α-17-one were added at 25° C. After stirring for 30 minutes, 50 ml of water were carefully added and the reaction mixture was separated and washed with water and sodium bicarbonate solution. The aqueous layer was extracted with toluene and the combined organic layers were evaporated in vacuo The resulting oil was added to a solution of 42 g of sodium bicarbonate in 65 ml of water and 175 ml of ethanol. After refluxing under a nitrogen atmosphere, the solid was filtered and washed with ethanol. The filtrate was concentrated, and water was carefully added. The crystallized compound was filtered, washed with ethanol/ water and filtered to obtain 4.12 g (78% yield) of 17β-1-(1-ethoxy-ethenyl)-Δ$^4$-androsten-14α,17α-ol-3-one.

NMR (CDCl$_3$): delta 0.803 (3H, s), 1.200 (3H, s), 1.32 (3H, tr), 3.64 (1H, s), 3.73 (2H, q), 4.07 and 4.30 (2H, 2×d), 4.64 (1H, s), 5.73 (1H, s).

EXAMPLE 15

7β-1-(1-ethylsulfenyl-ethenyl)-Δ$^4$-androsten-14a,17β-diol-3-one

To a solution of 0.47 g (5.34 mmol) of ethyl vinylsulfide in 20 ml of dry THF under a nitrogen atmosphere, 3 ml of 1.7M t-butyl-lithium in pentane were carefully added at −70° C. and after stirring for 1.5 hours at −75° C., the temperature was raised to 0° C. 0.33 g, (1 mmol) of solid 3-ethoxy The reaction mixture was stirred for 45 minutes at 0° C., after which 1 ml of water and 1 ml of concentrated aqueous hydrogen chloride solution were added. After stirring for 20 minutes, the reaction mixture was neutralized with a bicarbonate solution and was extracted with ethyl acetate. The organic layer was washed with a sodium chloride solution, filtered, dried and evaporated in vacuo to obtain 164 mg (42% yield) of 17β-1-(1-ethylsulfenyl-ethenyl)-Δ$^4$-androsten-14α,17α-diol-3-one.

$^1$H NMR (CDCl$_3$): delta 0.849 (3H, s), 1.207 (3H, s), 1.32 (3H, tr), 4.17 and 4.34 (2H, 2×s), 4.95 and 5.45 (2H, 2 x s), 5.72 (1H, s). The compound could be converted into Δ$^4$pregnene-14α,17α-diol-3,20-dione. Therefore, the experiment was repeated under the same conditions except that the reaction mixture was hydrolyzed for 1.5 hours to obtain a 66% yield (calculated on 3-ethoxy-Δ$^{3,5}$-androstadien-14α-ol-17-one. The NMR spectrum was identical with the product of Example 7.

EXAMPLE 16

17β-1-(1-phenylsulfinyl-ethyl)-Δ$^4$-androsten-14α,17α-diol-3-one

To a solution of 1 ml (7.08 mmol) of diisopropylamine in dry THF under a nitrogen atmosphere, 5.5 ml of 15% n-butyllithium in hexane were added over 10 minutes at −25° C. and after stirring for 5 minutes, a solution of 1.2 g (7.89 mmol) of phenylsulfinylethene in 4 ml of THF was added at −70° C. The reaction mixture was stirred for 15 minutes at −75° C. and the temperature was raised to −10° C. 0.5 g (1.52 mmol) of solid 3-ethoxy-Δ$^{3,5}$-androstadien-14α,-ol-17-one was added. The reaction mixture was stirred for 30 minutes at −20° C. after which 5 ml of water and 4 ml of concentrated aqueous hydrogen chloride solution were added. After stirring for 30 minutes and 0° C., the reaction mixture was extracted with ethyl acetage and the organic layer was washed with water and 1M sodium bicarbonate solution, dried and evaporated in vacuo. Chromatography over silica gel (toluene/ acetone 5/1) afforded the two isomers of 17β-1-(1-phenylsulfinyl-ethyl)-Δ⁴-androsten-14α,17ζ-diol-3-one (I: 220 mg. II: 140 mg).

ISOMER I: NMR (CDCl₃, CD₃OD): delta 0.88 (3H, s), 1.19 (3H, s), 4.46 (2H, s), 5.68 (2H, s), 6.07 and 6.37 (2H, 2×d), 7.4–7.8 (5H,m).

ISOMER II: NMR (CDCl₃, CD₃OD): delta 0.92 (3H, s), 1.26 (3H, s), 4.43 (2H, s), 5.71 (2H, s), 5.92 and 6.32 (2H, 2×d), 7.3–7.8 (5H, m).

EXAMPLE 17

14α,17α-Propylidenedioxy-17β-1-(1-phenylsulfinylethenyl)-Δ⁴-androsten-3-one

A solution of 100 mg (0.22 mmol) of 17β-1-(1-phenyl-sul-finylethenyl)-Δ⁴-androsten-14α,17α-diol-3-one (isomer I of Example 16 in 1 ml (25/40/0.15 v/v/v) of acetic acid/propanal/-concentrated sulfuric acid was stirred for 1.5 hours after which the reaction mixture was poured into a sodium bicarbonate solution and extracted with methylene chloride. The organic layer was washed with water and evaporated in vacuo. After crystallization from acetone/hexane, androsten-3-one were obtained NMR (CDCl₃): delta 0.92 (3H, tr), 0.924 (3H, s), 1.150 (3H, s), 4.75 (1H, tr), 5.73 (1H, s), 6.02 and 6.50 (2H, 2×d), 7.4–7.9 (5H, m).

The other isomer was prepared by the same procedure starting from isomer II of Example 16 to obtain 71 mg.

NMR (CDCl₃):delta 0.71 (3H, tr), 0.920 (3H, s), 1.200 (3H, s), 4.64 (1H, tr), 5.73 (1H, s), 5.87 and 6.48 (2H, 2×d), 7.3–7.8 (5H, m).

EXAMPLE 18

17α-methyl-Δ⁴-androsten-14α,17β-diol-3-one

A solution of 0.5 ml (8 mmol) of methyl iodide in 2 ml of dry diethyl ether was added under a nitrogen atmosphere to a stirred suspension of 195 mg of magnesium in 8 ml of diethyl ether. After addition of 0.5 g (1.58 mmol) of solid 3-ethoxy-Δ³,⁵-androstadien-14α-17-one, the reaction mixture was stirred at room temperature for 1.5 hours after which an aqueous ammonium chloride solution was added dropwise. The aqueous layer was extracted with methylene chloride and the combined organic layers were washed with water, dried over Na₂SO₄ and evaporated in vacuo. The crude product was hydrolyzed for 15 minutes in a mixture of 5 ml of acetone, 0.1 ml of water and 0.25 ml of concentrated hydrochloric acid, 25 ml of water were added and the precipitated solid was collected, washed with water and dried. Chromatography of the crude product over silica ge (toluene/acetone 6/1) yielded 32 mg of 17u-methyl-Δ⁴-androsten-14α,17β-diol-3-one.

NMR (CDCl₃): delta 1.044 (3H, s), 1.227 (3H, s), 1.509 (3H, s), 5.72 (1H, s).

EXAMPLE 19

3-Ethoxy-17β-methyl-Δ³,⁵-androstadiene-14α,17α-diol 7.5 ml of a solution of 1.5 M methyl lithium in dry diethyl-ether were added under a nitrogen atmosphere to a solution of 1.65 g of 3-ethoxy-Δ³,⁵-androstadien-14α-ol-17-one in 50 ml of dry THF at −70° C. After stirring for 1 hour, the temperature was raised to room temperature whereafter another 4 ml of methyllithium solution were added. After stirring for 1 hour, the reaction mixture was poured into 100 ml of water followed by extraction three times with 50 ml of methylsi-obutylketone. The combined organic layers were washed with water, dried and evaporated in vacuo. Chromatography of the crude product over silica gel (toluene/acetone 19/1) yield 152 mg of 3-ethoxy-17β-methyl-Δ³,⁵-androstadiene-14α,17α-diol melting at 180°-183° C. (dec.).

NMR (CDCl₃): delta 0.865 (3H, s), 1.102 (3H, s), 1.23 (3H, s), 1.30 (3H, t), 3.15+3.9, 3,8 (2H, q), 5.14 (1H, s), 5.27 (1H, t).

EXAMPLE 20

17β-ethyl-Δ⁴-androsten-14α,17α-diol-3-one (I) and 17α-ethyl-Δ⁴-androsten-14α,17β-diol-3-one (II)

A solution of 2.95 ml (40 mmol) of ethyl bromide in 5 ml of dry diethyl ether was added dropwise under a nitrogen atmosphere to a stirred suspension of 0.96 g of magnesium in 20 ml of dry diethyl ether. After refluxing for 0.5 hours, a suspension of 2.5 g (7.9 mmol) of 3-methoxy-Δ³,⁵-androstadien-14α-ol-17-one in 25 ml of dry THF was added dropwise. The reaction mixture was refluxed for 1.5 hours after which 50 ml of an aqueous 15% ammonium chloride solution were added dropwise at 20° C. The aqueous layer was extracted with methylene chloride after which the combined organic layers were washed with water, dried over Na₂SO₄ and evaporated in vacuo. The crude product was hydrolyzed in 45 minutes in a mixture of 25 ml of acetone, 0.5 ml of water and 0.5 ml of aqueous 6N hydrochloric acid. The reaction mixture was extracted with methylene chloride. The organic layer was washed with water and evaporated in vacuo. Chromatography of 2.5 g of the crude product over silica gel (toluene/ acetone 9/1) afforded a 3:7 mixture of the two isomers of 17β-ethyl-Δ⁴-androsten-14α,17α-diol-3-one (I) and 17α-ethyl-Δ⁴-androsten-14α, 17β-diol-3-one (II).

NMR (CDCl₃) isomer I: delta 0.884 (3H, s), 1.208 (3H, s), 0.97 (3H tr) 5.72 (1H, s); isomer II: delta 1.049 (3H, s), 1.222 (3H, s), 0.98 (3H, tr), 5.72 (1H, s).

EXAMPLE 21

17β-allyl-Δ⁴-androsten-14α,17α-diol-3-one

To a stirred suspension of 769 mg of magnesium and a crystal of iodine in 10 ml of dry THF under a nitrogen atmosphere, a solution of 1.37 (15.8 mmol) of alkyl bromide in 5 ml of dry THF was added dropwise in 45 minutes. After refluxing for 1 hour, 500 mg (1.58 mmol) of solid 3-methoxy-Δ³,⁵-androstadien-14α,-ol-17-one were added. The reaction mixture was refluxed for 2.5 hours after which 30 ml of an aqueous 15% ammonium chloride solution were added dropwise at 20° C. The aqueous layer was extracted with methylene chloride after which the combined organic layers were washed with water, dried over MgSO₄ and evaporated in vacuo. 0.6 g of the crude product was hydrolyzed in 30 minutes in a mixture of 5 ml of acetone, 0.1 mol of water and 0.1 ml of aqueous 6N hydrochloric acid. After 30 minutes, the reaction mixture was extracted with methylene chloride and the organic layer was washed with water and evaporated in vacuo. Chromatography over silica gel (toluene/acetone 7/1) yielded 170 mg of 17β-allyl-Δ⁴-androsten-14α,17α-diol-3-one.

NMR (CDCl₃): delta 0.921 (3H, s), 1.207 (3H, s), 2.35 (2H, d), 3.51 (S, 1H), 4.12 (S, 1H), 5.15 (2H, m), 5.72 (1H, s), 5.95 (1H, m).

Various modifications of the products and processes of the invention may be made without departing from the spirit or scope thereof and the invention is intended to be limited only as defined in the appended claims.

What we claim is:

1. A compound of the formula

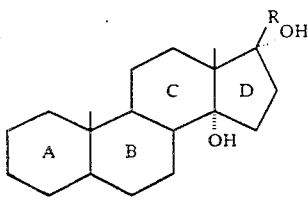

where R is selected from the group consisting of ethyl substituted at the 1 position by 'members of the group consisting of alkoxy, phenyloxy, alkylthio of 1 to 4 carbon atoms, phenylthio, alkylsulfinyl of 1 to 4 carbon atoms, phenylsulfinyl, alkylsulfonyl of 1 to 4 carbon atoms and phenylsulfonyl, or 1-cyano-1-(tri-$C_{1-4}$ alkyl) silyloxy, and ethyl substituted at the 1 position with an alkyleneoxythio of 1 to 4 carbon atoms, alkylenethiosulfoxy of 1 to 4 carbon atoms, or alkylenedithio of 1 to 4 carbon atoms, the phenyls being unsubstitued or substituted by a methyl and the A, B, C and D rings may contain one or more double bonds and are unsubstituted, substituted by one or more member of the group consisting of hydroxy, amino, oxygen, alkoxy and alkoxyalkoxy, or disubstituted by one or more members of the group consisting of alkylenedioxy, alkylenedithio, alkylenethiosulfoxy and alkyleneoxythio.

2. The compound of claim 1 wherein R is selected from the group consisting of ethynyl substituted at the 1-position with a substituent selected from the group consisting of alkoxy, phenyloxy, alkylthio of 1 to 4 carbon atoms, phenylthio, alkylsulfinyl of 1 to 4 carbon atoms, phenylsulfinyl, alkylsulfonyl of 1 to 4 carbon atoms and phenylsulfonyl, and phenyls being unsubstituted or substituted by methyl.

3. The compound of claim 1 wherein the A, B, C and D rings contain a double bound located between one or more carbon pairs selected from the group consisting of $C_1$ and $C_2$, $C_3$ and $C_4$, $C_5$ and $C_6$, $C_6$ and $C_7$, $C_9$ and $C_{11}$, and $C_{11}$ and $C_{12}$.

4. The compound of claim 1 wherein the A, B, C and D rings are disubstituted by a substituent selected from the group consisting of 3,3-alkylenedioxy, 3,3-alkylenedithio, 3,3-alkylenethiosulfoxy and 3,3-alkyleneoxythio, wherein the alkylene moieties contain p2 or 3 carbon atoms.

* * * * *